United States Patent [19]

Zehner et al.

[11] 4,005,128

[45] Jan. 25, 1977

[54] PROCESS FOR THE PREPARATION OF OXALATE ESTERS

[75] Inventors: Lee R. Zehner, Media, Pa.; Richard W. Sauer, deceased, late of Cherry Hill, N.J.; John J. Heffron, executor, Morrisville, Pa.

[73] Assignee: Atlantic Richfield Company, Los Angeles, Calif.

[22] Filed: Apr. 2, 1975

[21] Appl. No.: 564,242

[52] U.S. Cl. .................. 260/485 R; 260/465 D; 260/465.4; 260/485 H; 260/485 J; 260/485 L; 260/485 P

[51] Int. Cl.$^2$ .................................. C07C 69/36

[58] Field of Search ....... 260/485 R, 485 L, 485 H, 260/485 J, 485 P, 465.4, 465 D

[56] References Cited

UNITED STATES PATENTS 3,393,136  7/1968  Fenton et al. ............. 260/485 R

FOREIGN PATENTS OR APPLICATIONS 2,213,435  10/1973  Germany ............. 260/485 R Primary Examiner—Jane S. Myers
Attorney, Agent, or Firm—Delbert E. McCaslin

[57] ABSTRACT

A process for the preparation of oxalate esters by reacting carbon monoxide with an alcohol in the presence of a stoichiometric quantity of a metal salt catalyst and a stoichiometric quantity of an amine base. Preferably stoichiometric amounts of particular metal oxidizing salts are employed along with the metal salt catalyst and a stoichiometric amount of amine base. Alternatively ligands of the metal salt catalysts may be employed, especially in conjunction with a metal oxidant and an amine base thereby providing a pronounced effect on selectivity for the oxalate ester over the carbonate.

17 Claims, No Drawings

PROCESS FOR THE PREPARATION OF OXALATE ESTERS

BACKGROUND OF THE INVENTION

A number of prior art processes have been proposed for the preparation of oxalates and carbonates by oxidative carbonylation in the presence of alcohols including the use of metal salt catalysts, dehydrating agents and ferric or cupric redox agents in the solution.

The present invention is directed to an improved process for the preparation, in high yield, of oxalate esters, and exceeding the yield of carbonates. More particularly, it relates to the preparation of oxalates by reacting carbon monoxide with an alcohol under elevated temperature and pressure conditions in the presence of stoichiometric amount of palladium, rhodium, platinum, or copper salt catalyst and a stoichiometric amount of an amine base and includes the employment of iron (III) or copper (II) oxidant salts in addition to various counterions and ligands of the metal salt catalysts.

U.S. Pat. No. 3,114,762 discloses a method for the preparation of alkyl carbonates by reacting carbon monoxide with an alcohol in the presence of platinum or palladium chloride and in the added presence of an oxidizing salt for reoxidizing the catalyst in situ. The reaction is carried out at temperatures of from 20° to 100° C. and carbon monoxide pressures of 1 to 500 atmospheres. Runs carried out for comparison even at higher temperatures only resulted in trace amounts of the oxalate.

U.S. Pat. No. 3,393,136 describes a process for the preparation of oxalates by contacting carbon monoxide at superatmospheric pressure, with a saturated monohydric alcohol solution of a platinum group metal salt and a soluble ferric or cupric salt (redox agent) while maintaining the salts in a highly oxidized state by the simultaneous introduction of oxygen or the application of a direct current electrical potential to the reaction zone. When oxygen is employed, explosive mixtures of oxygen and combustible organic vapors in the gas phase must be avoided and water scavengers or dehydrating agents such as alkyl orthoformic acid esters must be added to the liquid phase to prevent the accumulation of water.

In a recent article by Donald M. Fenton and Paul J. Steinwand, Journal of Organic Chemistry, Vol. 39, No. 5, 1974, pp. 701–704, a general mechanism for the oxidative carbonylation of alcohols to yield dialkyl oxalates using a palladium redox system, oxygen and dehydrating agents has been proposed. In the absence of the necessary dehydrating agent, a large amount of carbon dioxide is formed and oxalates are not produced. The necessity of the iron or copper redox system during the oxalate synthesis is emphasized.

A recent West German Pat. No. 2,213,435 discloses a method for the synthesis of oxalic acid and oxalate esters in water and alcohol respectively. A platinum group metal salt, a salt of a metal more electropositive than the platinum group metal, e.g., copper (II) chloride and an alkali metal salt comprise the catalyst. Oxygen in stoichiometric amounts was employed as the oxidant. A disadvantage of such reaction is that explosive mixtures of oxygen and carbon monoxide are necessary to effect reaction. Under non-explosive conditions only trace amounts of oxalate can be obtained.

Many important commercial applications have been developed for the oxalate products of this invention, for example, as cellulose ether or ester and resin solvents, as dye intermediates and the preparation of pharmaceuticals.

The process of the present invention provides a high yield selectivity to the oxalate esters. Carbonate esters and carbon dioxide associated with such reactions are minimized by a critical regulation of the catalyst and oxidant anions and alternatively certain ligands and by maintaining the reaction mixture substantially anhydrous.

Other advantages of the present invention, as compared to known prior art processes are (1) elimination of hazardous operational conditions by avoiding explosive mixtures of oxygen and carbon monoxide, (2) avoiding any necessity for using dehydrating agents as no water is formed as a result of the instant oxidative carbonylation process; when air or $O_2$ are used as the oxidant water and $CO_2$ are formed and the presence of water always decreases the yield of oxalate and increases the $CO_2$; (3) avoiding the use of large amounts of corrosive chloride ions, (4) ease of recovery and reoxidation of the metal salts in a stream of air or oxygen for reuse in the oxidative carbonylation process and (5) the ability to employ in the process as catalysts the more readily available copper salts in place of the more expensive platinum group metal salts.

SUMMARY OF THE INVENTION

According to the present invention there is provided a much improved oxidative carbonylation process for the preparation in high yield of oxalates by reacting carbon monoxide with an alcohol, which process is carried out at elevated temperatures and pressures in the presence of a metal salt catalyst and under relatively anhydrous conditions.

It has been found that the above-mentioned reaction can be carried out at high conversions to the oxalate ester, over the carbonate which may be present in only trace amounts, by conducting the reaction in the presence of a stoichiometric quantity of an amine and that stoichiometric quantities of oxidizing salts may also be employed with the amines to provide a pronounced effect on oxalate ester selectivity. In addition, it has been found that alternatively catalytic amounts of various ligands, which will not work in themselves, may be used as co-catalysts in conjunction with the metal salt catalysts, the amines and the oxidant salts, the amines and oxidant salts being employed in the proper stoichiometric quantities.

It is a primary object of this invention to provide a process for the preparation of oxalate esters in high yield while avoiding operational problems associated with prior processes.

It is another object of this invention to provide a novel reaction system useful in the conversions of carbon monoxide and alcohol to oxalate esters.

It is a further object of this invention to provide a specific mechanism for the employment of catalysts, oxidant and an amine in an oxidative carbonylation process.

A further object is to provide an improved process for the preparation of commercially important diethyl or diisopropyl oxalate.

These and other objects and advantages of this invention will become apparent from the description of the invention which follows and from the claims.

DESCRIPTION OF THE INVENTION

In accordance with this invention, an oxalate ester is produced by reacting, under relatively anhydrous liquid phase conditions, an alcohol with carbon monoxide at elevated temperatures and pressures in the presence of a catalyst comprising a palladium, rhodium, platinum or copper salt, with or without a ligand of the catalyst as a co-catalyst, and a stoichiometric amount of an amine and preferably, in the presence of stoichiometric amounts of a metal oxidant such as a copper (II) or iron (III) salt along with a catalytic amount of the above metal salt catalyst and the amine.

A general postulated equation for the reaction may be represented as follows:

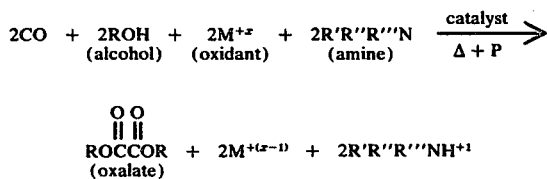

wherein R is selected from monohydric substituted or unsubstituted aliphatic, alicyclic or aromatic groups, M is a metal oxidant salt and $x$ may be 2 or 3, R', R" and R''' may be hydrogen, or a substituted or unsubstituted, aliphatic, aromatic, cycloaliphatic or heterocyclic group. In the reaction the amine, employed in stoichiometric amounts, functions as a hydrogen ion acceptor.

The reaction between the alcohol, carbon monoxide and amine may be carried out in an autoclave or any other high pressure reactor. A general procedure is to charge the alcohol, amine, catalyst and in the preferred embodiment, the oxidant into the reactor vessel, introduce the proper amount of carbon monoxide to obtain the desired reaction pressure and then heat the mixture to the desired temperature for the appropriate period. The reaction can be carried out batchwise or as a continuous process and the order of addition of the reactants may be varied to suit the particular apparatus employed. The reaction products are recovered and treated by any conventional method such as filtration, etc. to effect separation of the oxalate from unreacted materials, catalyst, oxidant, by-products, etc.

The reaction is performed and takes place under relatively anhydrous conditions, i.e., in an essentially anhydrous alcoholic media. The alcohols suitable for use in the process of the present invention can be monohydric saturated aliphatic and alicyclic alcohols or aromatic alcohols and may contain other substituents such as halo, amido, alkoxy, amino, carboxy, cyano, etc. radicals in addition to the hydroxyl group. The substituents, in general, do not interfere with the reaction of the invention.

The alcohols which may be primary, secondary or tertiary alcohols conform to the general formula ROH wherein R is an optionally substituted aliphatic or alicyclic group preferably containing from 1 to 20 carbon atoms. R may also be an aromatic group containing one or more benzenoid rings preferably not more than 3 rings which may be fused or joined by single valency bonds, directly or through bridging groups which may be, for example, oxygen or sulfur atoms or sulfoxide, sulfone or carbonyl groups or alkylene groups in which, if desired, the carbon chain may be interrupted by, for example, oxygen or sulfur atoms, sulfoxide, sulfone or carbonyl groups, for example methylene, oxymethylene, dimethylene sulfone or dimethylene ketone groups. Representative alcohols especially suitable for use in this invention are monohydric alcohols such as methyl, ethyl, n-, iso-, sec-, and tert-butyl, amyl, hexyl, octyl, lauryl, n- and sec- propyl, cetyl, benzyl, chlorobenzyl and methoxy-benzyl alcohols as well as, for example, cyclohexanol, octanols, heptanols, decanols, undecanols, 2 ethyl hexanol, nonanol, myristyl alcohol, stearyl alcohol, methyl cyclohexanol, pentadecanol, oleyl and eicosonyl alcohols, and the like. The preferred alcohols are the secondary monohydric alcohols, such as 2-propanol.

The amines employed in the process of the invention which may be ammonia or primary, secondary or tertiary amines include aliphatic, cycloaliphatic, aromatic and heterocyclic amines or mixtures therof. The amines may be unsubstituted or contain other substituents such as halides, alkyl, aryl, hydroxy, amino, alkylamino, carboxy, etc.

Representative amines, as hereinabove described, include for example, mono-, di- and tri-methyl, ethyl, and propyl amines, iso- and diiso-propyl amines, allyl amines, mono-, di-, tri-, iso- and diisobutyl amines, 1-methylpropyl amine, 1,1-dimethyl-ethyl amine, amyl amines, cyclohexyl amine, dicyclohexylamine, 1,3-dimethylbutyl amine, 2-ethylhexylamine, 1-cyclopentyl-2-aminopropane, 1,1,3,3-tetramethylbutylamine, aniline, ethylene diamine, methylene diamines, ethanolamines, octylamines, n-decylamine, do-, tetra-, hexa-, octa-, dido-, ditetra-, diocta-, trido- and trioctadecyl amines, aniline, chloroanilines, nitroanilines, toluidines, naphthylamines, N-methyl and N-ethyl, and N,N-dimethyl and N,N-diethyl aniline, di- and triphenylamines, N,N-diamylaniline, benzyl dimethyl amine, piperidine, pyrrolidine, etc. The preferred amines are the tertiary amines such as triethylamine.

The metal salt catalysts which may be employed in the process of this invention are the palladium (II), platinum (II), rhodium (III), copper (II) or copper (I) salts. Among the chemical forms of the metal compounds which can be used are the pallidium, platinum and rhodium, halides, sulfates, oxalates and acetates and the copper halides preferably the palladium (II) and copper (I) or (II) halides such as palladium (II) chloride and copper (II) chloride. Representative catalytic metal salt compounds include, for example, palladium (II) chloride, copper (II) chloride, rhodium (III) chloride, copper (II) iodide, palladium (II) sulfate, palladium (II) oxalate, palladium (II) acetate, palladium (II) iodide, rhodium (III) bromide, platinum (II) chloride, platinum (II) sulfate, etc.

The reaction is generally carried out in the presence of a stoichiometric proportion of the metal salt catalyst in the absence of the additon of oxidant, and will proceed with small amounts of the metal salt catalyst compounds herein above described when an oxidant is added to reaction mixture. Generally the proportions of the metal salt catalyst used in the reaction will be equivalent to between about 0.01 to 10 weight percent of the alcohol employed. When the reaction is carried out in the presence of an oxidant salt the metal salt catalyst is preferably employed in amounts between about 0.01 to 2 percent by weight of the alcohol employed.

As mentioned hereinabove, a ligand or co-ordination complex compound of the metal catalyst may be employed in the process of the invention as a co-catalyst and thereby also achieve a pronounced increase in the selectivity for the oxalate ester. The ligands may be, for example, alkyl or aryl phosphines, arsines or stibines. The complexes of the metal catalysts which are suitable as co-catalysts in the process of the present invention include complex compounds of palladium, platinum, rhodium and copper. The complex compounds may contain one or more atoms of the said metals in the molecule and when more than one such atom is present, the metals may be the same or different. The mono- or poly-dentate ligands which are present in the molecule of the complex compounds and in which at least one of the electron-donating atoms is an atom of phosphorous, arsenic or antimony containing a lone pair of electrons may be, for example, organo-phosphines, -arsines and -stibines. Suitable mono-dentate ligands include alkyl phosphines such as trimethylphosphine and tributylphosphine, aryl-phosphines such as triphenylphosphine, mixed alkylaryl phosphines such as diethylphenylphosphine and radicals derived from such phosphines, for example the radical having the formula—$P(CH_3)_2$. Hydrocarbyloxy phosphines, i.e., phosphites, such as triphenyl phosphite may also be employed. Suitable polydentate ligands include tetramethyl diphosphinoethane and tetraphenyl diphosphinoethane. Exactly analogous derivatives of arsenic and antimony may be used; however, because of their greater ease of preparation and stability of the derived complexes, the hydrocarbyl derivatives of phosphorus are preferred.

The complex compounds suitable for use in the process of the present invention may contain in the molecule, in addition to the ligands discussed above, one or more other atoms, groups or molecules, which are chemically bonded to the metal atom or atoms. Atoms which may be bonded to the metal include, for example, hydrogen, nitrogen and halogen atoms; groups which may be bonded to the metal include, for example hydrocarbyl, hydrocarbyloxy, carbonyl, nitrosyl, cyano and $SnCl_3$—groups; molecules which may be bonded to the metal include, for example, organic isocyanides and isothiocyanates.

Examples of suitable complex compounds are those represented by the following formulae:

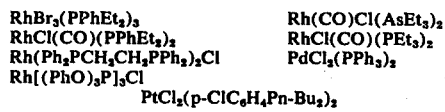

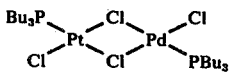

The complex compounds employed may be introduced into the reaction mixture as such, or they may be formed in situ from a suitable metal compound noted above and the desired ligand.

The complex compounds may be used in catalytic amounts of from 0.001 to 5 percent preferably from 0.01 to 2 percent by weight of the alcohol to be reacted although larger or smaller amounts may be employed at varied pressures or reaction rates.

The oxidizing salts which are employed in an anhydrous condition and in stoichiometric amounts in the process of the invention include the iron (III) and copper (II) salts such as the sulfates, trifluroacetates, oxalates, or acetates preferably the iron (III) or copper (II) sulfates and trifluoroacetates. Representative oxidant salts include, for example, copper (II) sulfate, iron (III) sulfate, copper (II) trifluroracetate, copper (II) acetate, copper (II) oxalate, iron (III) acetate and iron (III) oxalate, and iron (III) trifluoroacetate. Unsuitable for use as oxidants in the present invention are the redox metal chlorides, i.e., the ferric or cupric chlorides which form the metal catalyst redox oxidant system. The redox metal chloride salts system is not operative in the method of the present invention. Excess chlorides are detrimental to the reaction system of the present invention.

The process of the invention can be operated entirely under the liquid phase conditions of the anhydrous alcohol and amine. Although not required, solvents, if desired, which are chemically inert to the components of the reaction system may be employed. Suitable solvents include, for example, organic esters such as ethyl acetate, n-propyl formate, isopropyl acetate, sec- and iso-butyl acetate, amyl acetate, cyclohexyl acetate, n-propyl benzoate, lower alkyl phthalates, etc., and the alkyl sulfones and sulfoxides such as propyl ethyl sulfoxide, diisopropyl sulfone diisooctyl sulfoxide, etc.

As indicated above the reaction can be suitably performed by introducing the carbon monoxide at a desired pressure into contact with the alcoholic reaction medium containing the specified reactants and catalysts and heating to the desired temperature. In general, a carbon monoxide pressure of about 1 to about 700 atmospheres, preferably from about 100 to 200 atmospheres are employed as total reaction pressure. Stoichiometric quantities of carbon monoxide are generally employed. However, an excess of carbon monoxide may be employed, for example, in continuous processes where a large excess of or high carbon monoxide requirements are generally utilized, a suitable recycle of the carbon monoxide may be employed. The reaction will proceed at temperatures of from about 50° to 250° C. It is generally preferred to operate the process at temperatures in the range of 100° to 125° C. to obtain a convenient rate of reaction. Heating and/or cooling means may be employed interior and/or exterior of the reaction to maintain the temperature within the desired range.

The reaction time is generally dependent upon the alcohol being reacted, temperature, pressure and on the amount and type of catalyst and oxidant being charged as well as the type of equipment being employed. Usually between ½ hour and 4 hours at reaction temperatures and pressures are required to obtain the desired degree of reaction but shorter or longer reaction times may be employed. Reaction times will vary dependent on whether the process is continuous or batch.

The following examples are provided to illustrate the invention in accordance with the principles of this invention but are not to be construed as limiting the invention in any way except as indicated by the appended claims.

In the runs which follow a 300 ml. stainless steel stirred autoclave was employed and the reaction products were analyzed by gas-liquid phase chromatography for the oxalate and carbonate.

EXAMPLE I

Into the autoclave was charged 3.72 g. of palladium (II) chloride, 9.00 g. of 1,8-bis-(dimethylamino)-naphthalene, and 52 ml. of absolute ethanol. The mixture was purged with a slow stream of nitrogen for 10 minutes. 1800 psi of CO was introduced with stirring. The reaction mixture was heated to 125° C. for 2 hours. The autoclave was cooled and opened. The reaction product was filtered to give 40.8 g. of reddish-brown liquid filtrate. Quantitative glc analysis indicated the presence of 0.53 g. of diethyl oxalate and 0.57 of diethyl carbonate.

EXAMPLE II

The procedure of Example I was repeated with a reaction mixture of 0.25 g. of palladium (II) chloride, 14.80 g. of anhydrous copper (II) sulfate, 4.67 g. of triethylamine, and 70 ml. of absolute ethanol. The reaction temperature of 125° C. held for 105 minutes. The reaction product was filtered to give 53.6 g. of dark brown liquid filtrate, which contained 1.45 g. of diethyl oxalate and 1.12 g. of diethyl carbonate.

EXAMPLE III

The procedure of Example I was repeated with a reaction mixture of 0.25 g. of palladium (II) chloride, 18.49 g. of anhydrous iron (III) sulfate, 4.67 g. of triethylamine, and 70 ml. of absolute ethanol. The reaction temperature of 125° C. was maintained for 62 minutes. Vacuum filtration of the reaction product yielded 42.5 g. of golden brown liquid filtrate. The filtrate contained 2.25 g. of diethyl oxalate and 1.06 g. of diethyl carbonate.

EXAMPLE IV (Comparative)

The previous experiment was repeated using a reaction mixture consisting of 0.25 g. of palladium (II) chloride 12.44 g. of anhydrous copper (II) chloride, 4.67 g. of triethylamine, and 70 ml. of absolute ethanol. A reaction temperature of 125° C. was maintained for 105 minutes. Filtration of the reaction product gave 53.1 g. of orange-brown liquid which contained only a trace amount of diethyl oxalate and 2.28 g. of diethyl carbonate.

EXAMPLE V

The previous experiment was repeated with a reaction mixture of 1.00 g. dichlorobis-(triphenylphosphine)-palladium (II), 14.80 g. of anhydrous copper (II) sulfate, 9.34 g. of triethylamine, an 70 ml of absolute ethanol. The reaction temperature of 125° C. was maintained for 65 minutes. 76.2 g. of dark green liquid was obtained by vacuum filtration of the reaction product. The filtrate contained 3.39 g. of diethyl oxalate and 0.28 g. of diethyl carbonate.

EXAMPLE VI

The previous experiment was repeated with the same reaction mixture except that the ethanol was replaced with 70 ml. of 2-propanol. A reaction temperature of 125° C. was maintained for 71 minutes. 77.5 g. of green liquid product was obtained by vacuum filtration of the reaction product. The liquid filtrate contained 6.22 g. of diisopropyl oxalate and only a trace amount of diisopropyl carbonate.

EXAMPLE VII

The previous experiment was repeated with a reaction mixture of 0.38 g. of anhydrous copper (II) chloride, 0.75 g. of triphenyl phosphine, 14.80 g. of anhydrous copper (II) sulfate, 9.34 g. of triethylamine, and 70 ml. of 2-propanol. A reaction temperture of 125° C. was maintained for 142 minutes. The liquid filtrate from the reaction product weighed 74.2 g. and contained 3.55 g. of diisopropyl oxalate as well as a small amount of diisopropyl carbonate.

EXAMPLE VIII

The previous experiment was repeated with a reaction mixture of 0.30 g. of rhodium (III) chloride, 14.80 g. of anhydrous copper (II) sulfate, 4.67 g. of triethylamine, and 70 ml. of absolute ethanol. A reaction temperature of 125° C. was held for 73 minutes. The liquid reaction product contained diethyl oxalate and a small amount of diethyl carbonate.

EXAMPLE IX

The previous experiment was repeated with a reaction mixture of 1.00 g. of dichlorobis-(triphenylphosphine)-palladium (II), 14.80 g. of anhydrous copper (II) sulfate, and 74 ml. of 1.25 molar ammonia in absolute ethanol. A reaction temperature of 125° C. was maintained for 170 minutes. The reaction mixture was separated by vacuum filtration. The filtered solid was extracted with several portions of hot absolute ethanol. The combined filtrates were found by quantitative glc to contain 2.19 g. of diethyl carbonate.

EXAMPLE X

The previous experiment was repeated with a reaction mixture of 0.38 g. of anhydrous copper (II) chloride, 14.80 g. of anhydrous copper (II) sulfate, and 74 ml. of 1.25 molar ammonia in absolute ethanol. A reaction temperature of 125° C. was held for 60 minutes. Vacuum filtration of the reaction mixture gave 48.1 g. of light green liquid filtrate, which was found to contain 0.16 g. of diethyl oxalate in addition to 0.09 g. of diethyl carbonate.

EXAMPLE XI

The procedure of Example IX were repeated except the reaction temperature was increased to 160° C. for 86 minutes. The reaction product was filtered, and the solid residue was washed with several portions of hot absolute ethanol. The combined liquid filtrates (103.95 g.) were analyzed by glc after sitting at ambient temperature for one week. The filtrate contained 0.88 g. of diethyl oxalate and 0.22 g. of diethyl carbonate. A copious amount of a light blue solid containing copper (II) oxalate precipitated during this time. Copper (II) carbonate was not detected in the precipitate.

EXAMPLE XII

Into the autoclave was charged 0.25 g. palladium (II) chloride, 0.75 g. triphenylphosphine, 30.25 g. anhydrous copper (II) trifluoroacetate, 9.34 g. triethylamine, and 70 ml. 2-propanol. The mixture was purged with a slow stream of nitrogen for 10 minutes. 2000 psi CO was introduced with stirring. The reaction mixture was heated to 50° C. for 80 minutes. The autoclave was cooled and opened. The reaction product was filtered and the solid was washed in 2-propanol to give 91.2 g. of dark green liquid filtrate. Quantitative glc analysis indicated the presence of 1.93 g. diisopropyl oxalate and 0.67 g. diisopropyl carbonate.

EXAMPLE XIII

Into the stirred autoclave was charged a reaction mixture of 0.25 g. palladium (II) chloride, 0.75 g. triphenylphosphine, 16.80 g. anhydrous copper (II) acetate, 9.34 g. triethylamine and 70 ml. absolute 2-propanol. Nitrogen was purged through the reactor. CO was charged at 1800 psi. The reaction mixture was heated to 55° C. for 95 minutes. The reaction product was filtered to give 64.3 g. of green liquid filtrate, which contained 2.91 g. diisopropyl oxalate and a trace of diisopropyl carbonate.

EXAMPLE XIV

A mixture of 1.00 g. dichlorobis-(triphenylphosphine)-palladium (II), 14.00 g. copper (II) oxalate, 9.34 g. triethylamine, and 70 ml. 2-propanol was charged into the autoclave. A 10 minute nitrogen-purge was made. CO was charged to 1800 psi. Reaction temperature was held at 125° C. for 180 minutes. Diisopropyl oxalate was detected by glc analysis in the reaction product. No diisopropyl carbonate was detected.

EXAMPLE XV

A mixture of 0.70 g. dichlorobis-(triphenylphosphine)-palladium (II), 9.80 g. anhydrous copper (II) sulfate, 6.12 g. triethylamine, and 70 ml. t-butyl alcohol was charged into the autoclave. A 10 minute nitrogen-purge was performed. 1800 psi CO was charged, and the reaction temperature was held at 125° C. for 81 minutes. A significant amount of di-t-butyl oxalate was detected in the reaction product by glc analysis. Only a trace amount of di-t-butyl carbonate was detectible.

EXAMPLE XVI

The reaction mixture charged to the autoclave consisted of 0.25 g. palladium (II) chloride, 0.75 g. triphenylphosphine, 14.80 g. anhydrous copper (II) sulfate, 8.16 g. aniline, and 70 ml. absolute 2-propanol. The reactor was purged with nitrogen. CO was charged to 1800 psi, and the reaction temperature was held at 125° C. for 60 minutes. Diisopropyl oxalate was detected in the filtered reaction mixture while no diisopropyl carbonate was detectible.

EXAMPLE XVII

The procedure of Example XVI was repeated, except that the aniline was replaced with diethylamine (6.77 g.), and the reaction temperature (125° C.) was held for 88 minutes. Vacuum filtration of the brown slurry gave 17.5 g. of liquid, which by glc analysis contained 0.75 g. diisopropyl oxalate and 0.22 g. diisopropyl carbonate.

EXAMPLES XVIII, XIX, AND XX

Into the autoclave was charged 0.25 g. palladium (II) chloride, a weighed amount of ligand (see below), 14.80 g. copper (II) sulfate, 9.34 g. triethylamine, and 70 ml. absolute 2-propanol. CO was charged to 1800 psi. The reaction temperature was held at 125° C. for 1 hour, a period longer than necessary for complete CO consumption. The yields of products were:

| Ligand | Yield diisopropyl carbonate (g) | Yield diisopropyl oxalate (g) |
|---|---|---|
| Triethylphosphine | 0.37 | 4.30 |
| Triphenylarsine | 0.21 | 5.56 |
| Triphenylstibine | 0.77 | 2.30 |

EXAMPLE XXI

A mixture of 0.29 g. palladium (II) sulfate, 14.80 g. copper (II) sulfate, 4.67 g. triethylamine, and 70 ml. absolute ethanol was charged into the autoclave. The reactor was purged with nitrogen and then charged with 1800 psi CO. A temperature of 125° C. was maintained for 81 minutes. The reactor was cooled to room temperature. The reaction mixture was filtered to give 47.0 g. of liquid containing 1.2 g. diethyl carbonate and 0.6 g. diethyl oxalate. Only one-half the stoichiometric amount of triethylamine was employed.

EXAMPLE XXII

The procedure of Example XXI was repeated with 0.27 g. palladium (II) oxalate in place of palladium (II) sulfate. The filtered reaction mixture (49.1 g.) contained 0.9 g. diethyl carbonate and 0.3 g. diethyl oxalate. Only one-half the stoichiometric amount of triethylamine was employed.

EXAMPLE XXIII

A mixture of 0.63 g. palladium (II) acetate, 29.60 g. anhydrous copper (II) sulfate, 18.68 g. triethylamine, and 70 ml. absolute ethanol was charged into the autoclave. A nitrogen purge was made, and CO was charged to 1800 psi. The reaction temperature (125° C.) was maintained for 72 minutes. Glc analysis of the filtered reaction product showed the presence of diethyl carbonate and diethyl oxalate.

EXAMPLE XXIV

A mixture of 0.51 g. palladium (II) iodide, 0.75 g. triphenylphosphine, 14.80 g. anhydrous copper (II) sulfate, 9.34 g. triethylamine, and 70 ml. 2-propanol was charged into the autoclave. A 10 minute nitrogen-purge of the reactor was made. CO was charged to 1800 psi. The reaction temperature (125° C.) was held for 80 minutes. The reactor was cooled to room temperature. The reaction product was filtered to yield 69.3 g. of dark green liquid. Analysis showed the presence of 0.16 g. diisopropyl carbonate and 6.57 g. diisopropyl oxalate.

EXAMPLE XXV (Comparative)

This run carried out according to West German Pat. No. 2,213,435, Example I, except that non-explosive conditions were employed shows that only trace amounts of oxalate are obtainable using such conditions.

A mixture of 0.30 g. palladium chloride, 0.15 g. of lithium chloride and 2.0 g. of copper (II) chloride as a mixed solid were charged into 100 ml. of methanol into the autoclave. 300 psi of compressed air was charged to the reactor and the pressure increased to 1450 psi with carbon monoxide. The reaction temperature was increased from 60° to 100° C. over a period of 4 hours. The reaction product was filtered to yield 62.1 g. of brown liquid. Analysis detected only trace amounts of dimethyl oxalate.

EXAMPLE XXVI

A mixture of 0.27 g. of copper (I) iodide, 0.74 g. of triphenylphosphine, 14.80 g. anhydrous copper (II) sulfate, 9.34 g. triethylamine and 70 ml. of anhydrous 2-propanol was charged into the autoclave. Carbon monoxide was charged to 1800 psi and a reaction temperature of 135° C. held for 95 minutes. The reactor was cooled to room temperature and the reaction product filtered. Glc analysis showed a yield of 6.29 g. diisopropyl oxalate and 0.14 g. diisopropyl carbonate.

We claim:

1. A process for the preparation of oxalate esters of an alcohol having from 1 to 20 carbon atoms which comprises reacting under substantially anhydrous conditions, a saturated monohydric aliphatic or alicyclic alcohol which may contain other substituents which do not interfere with the reaction or an aromatic alcohol selected from the group consisting of benzyl, chlorobenzyl and methoxy-benzyl alcohols with carbon monoxide at a pressure of between about 1 and 700 atmospheres and at a temperature in the range of about 50° to 250° C. in the presence of an effective amount of a catalyst selected from the group consisting of palladium (II), rhodium (III), platinum (II) and copper (I) or (II) salt compounds and at least a stoichiometric amount of an aliphatic, cycloaliphatic, aromatic or heterocyclic amine or ammonia and at least a stoichiometric amount of a copper (II) or iron (III) oxalate, sulfate, acetate, or trifluroacetate oxidant salt compound and recovering the desired oxalate ester.

2. A process according to claim 1 wherein the oxidant salt compound is selected from the group consisting of copper (II) sulfate, copper (II) acetate, copper (II) oxalate, copper (II) trifluoroacetate, and iron (III) sulfate.

3. A process according to claim 2 wherein the oxidant salt compound is copper (II) sulfate.

4. A process according to claim 1 wherein the reaction is carried out in the present of a co-catalytic amount of an organic mono- or poly-dentate ligand selected from the group consisting of alkyl, aryl and halogen substituted phosphines, arsines and stibines.

5. A process according to claim 4 wherein the ligand is selected from the group consisting of triethylphosphine, triphenylphosphine, triphenylarsine and triphenylstibine.

6. A process according to claim 1 wherein the alcohol is selected from the group consisting of ethyl alcohol, isopropyl alcohol and tert-butylalcohol.

7. A process according to claim 1 wherein the catalyst is selected from the group consisting of palladium (II) chloride, palladium (II) sulfate, palladium (II) oxalate, palladium (II) acetate, palladium (II) iodide, copper (II) chloride, rhodium (III) chloride, and copper (I) iodide.

8. A process according to claim 7 wherein the catalyst is palladium (II) chloride.

9. A process according to claim 7 wherein the catalyst is copper (I) iodide.

10. A process according to claim 1 wherein the amine is selected from the group consisting of aniline, triethylamine, diethyl amine and 1,8-bis(dimethylamino) naphthalene.

11. A process according to claim 10 wherein the amine is triethylamine.

12. A process according to claim 1 wherein the pressure is between about 100 and 200 atmospheres and the temperature is in the range of about 100° to 125° C.

13. A process for the preparation of oxalate esters of an alcohol having from 1 to 20 carbon atoms which comprises reacting under substantially anhydrous conditions a saturated monohydric aliphatic or alicyclic alcohol which may contain other substituents which do not interfere with the reaction or an aromatic alcohol selected from the group consisting of benzyl, chlorobenzyl, and methoxy-benzyl alcohols with carbon monoxide at a pressure of between about 1 and 700 atmospheres and at a temperature in the range of about 50° to 250° C. in the presence of an effective amount of a catalyst selected from the group consisting of a palladium (II), rhodium (III), platinum (II) halide, sulfate, oxalate, or acetate and a copper (I) or copper (II) halide, at least a stoichiometric amount of an aliphatic, cycloaliphatic, aromatic or heterocyclic amine or ammonia, and at least a stoichiometric amount of an oxidant salt compound selected from the group consisting of a copper (II) or iron (III) oxalate, sulfate, acetate, or trifluroacetate, and recovering the desired oxalate ester.

14. A process according to claim 13 wherein the pressure is between about 100 and 200 atmospheres and the temperature is in the range of about 100° to 125° C.

15. A process according to claim 13 wherein a triphenylphosphine, arsine or stibine ligand is added to the reaction mixture.

16. A process according to claim 13 wherein the alcohol is isopropyl alcohol, the catalyst is palladium (II) chloride, the amine is triethylamine and the oxidant salt compound is copper (II) sulfate.

17. A process according to claim 13 wherein the alcohol is ethyl alcohol, the catalyst is palladium (II) chloride, the amine is triethylamine and the oxidant salt compound is copper (II) sulfate.

* * * * *